United States Patent [19]

Midha et al.

[11] Patent Number: 5,919,879
[45] Date of Patent: Jul. 6, 1999

[54] LINEAR TOUGHENED SILICONE GRAFTED POLYMERS

[75] Inventors: Sanjeev Midha, Blue Ash; Sean Patrick McDonough, Cincinnati, both of Ohio

[73] Assignee: The Procter & Gamble Company, Cincinnati, Ohio

[21] Appl. No.: 08/842,954

[22] Filed: Apr. 25, 1997

[51] Int. Cl.⁶ .................................... C08F 30/08
[52] U.S. Cl. ...................... 526/279; 424/70.12
[58] Field of Search .................. 526/279; 424/70.12

[56] References Cited

U.S. PATENT DOCUMENTS

| | | | |
|---|---|---|---|
| 4,693,935 | 9/1987 | Mazurek | 428/352 |
| 5,061,481 | 10/1991 | Suzuki et al. | 424/63 |
| 5,229,435 | 7/1993 | Sakai et al. | 523/105 |

*Primary Examiner*—Margaret G. Moore
*Attorney, Agent, or Firm*—Stephen T. Murphy

[57] ABSTRACT

Disclosed are linear toughened silicone grafted polymers useful in personal care compositions and the like.

8 Claims, No Drawings

LINEAR TOUGHENED SILICONE GRAFTED POLYMERS

TECHNICAL FIELD

The present invention relates to linear toughened silicone grafted polymers.

BACKGROUND OF THE INVENTION

Cosmetic compositions such as lotions, creams, emulsions, packs, make-up (e.g., foundations, lipsticks, eye shadows and the like) and hair compositions are used to improve one's outward appearance. Many personal care products use contain various resins, gums, and adhesive polymers. The polymers are used for a variety of purposes including thickening, feel properties, film-forming ability, active deposition, active penetration, hair holding, etc. Consequently there is constantly a search for developing polymers having improved properties for use in personal care product. Many of these compositions require the use of adhesive silicone grafted polymers. For example, the desire to have the hair retain a particular shape is widely held. The most common methodology for accomplishing this is the application of a styling composition to dampened hair, after shampooing and/or conditioning, or to dry, styled hair. These compositions provide temporary setting benefits and they can be removed by water or by shampooing. The materials used in the compositions to provide the setting benefits have generally been resins and have been applied in the form of mousses, gels, lotions or sprays.

Many people desire a high level of style retention, or hold, from a hair spray composition. In typical hair sprays, hold is achieved by the use of resins, such as AMPHOMER$^R$, supplied by National Starch and Chemical Company, and GANTREZ$^R$ SP 225, supplied by GAF. In general, as hair hold for hair spray compositions is increased, the tactile feel of the hair becomes stiffer and hence, less desirable. It is desirable to provide hair spray products which could provide an improved combination of hair hold and hair feel characteristics.

Recently, it has become known to utilize silicone grafted organic backbone polymers in various personal care compositions including their use as hair setting agents in hairspray compositions and other hair styling compositions, e.g. hair tonics, lotions, rinses, mousses, etc. Silicone grafted polymers can be used to make personal care compositions with improved feel, e.g., in the case of hair sprays, increased softness relative to conventional polymeric hair setting agents.

However, it remains desirable to improve the performance of these silicone grafted polymers. It is an object of this invention to provide such linear toughened silicone graft copolymers which can be used in, for example, personal care compositions.

It is a further object of this invention to provide linear toughened silicone graft copolymers that have improved adhesive and cohesive properties.

These and other benefits as may be apparent from the description below can be obtained by the present invention.

The present compositions can comprise, consist of, or consist essentially of any of the required or optional ingredients and/or limitations described herein.

All percentages and ratios are calculated on a weight basis unless otherwise indicated. All percentages are calculated based upon the total composition unless otherwise indicated.

All ingredient levels are refer to the active level of that ingredient, and are exclusive of solvents, by-products, or other impurities that may be present in commercially available sources, unless otherwise indicated.

SUMMARY OF THE INVENTION

The present invention relates to a personal care composition comprising: polymer for use in personal care compositions comprising a silicone grafted adhesive polymer, said polymer being characterized by an organic polymeric backbone wherein said backbone comprises (a) at least one monomer wherein when said monomer is polymerized as a homopolymer having a Tg of from about −120° C. to about 25° C. and (b) at least one monomer wherein when said monomer is polymerized as a homopolymer having a Tg of from above about 25° C. to about 250° C.

wherein said silicone grafted adhesive polymer has silicone macromers grafted to said backbone and wherein the number average molecular weight of said silicone macromers is greater than about 1000.

DETAILED DESCRIPTION OF THE INVENTION

The essential components of the present invention are described below. Also included is a nonexclusive description of various optional and preferred components useful in embodiments of the present invention.

Silicone Grafted Adhesive Polymer

The present invention relates to a silicone grafted adhesive polymer, said polymer being characterized by an organic polymeric backbone wherein said backbone comprises:

(a) at least one monomer wherein when said monomer is polymerized as a homopolymer having a Tg of from about −120° C. to about 25° C. and (b) at least one monomer wherein when said monomer is polymerized as a homopolymer having a Tg of from above about 25° C. to about 250° C.

wherein said silicone grafted adhesive polymer has silicone macromers grafted to said backbone and wherein the number average molecular weight of said silicone macromers is greater than about 1000.

By adhesive polymer what is meant is that when applied as a solution to a surface and dried, the polymer forms a film or a weld. Such a film will have adhesive and cohesive strength, as is understood by those skilled in the art.

The silicone grafted polymers are characterized by polysiloxane moieties covalently bonded to and pendant from a polymeric carbon-based backbone.

The backbone will preferably be a carbon chain derived from polymerization of ethylenically unsaturated monomers. The backbone comprises (a) at least one monomer wherein when said monomer is polymerized as a homopolymer having a Tg of from about −120° C. to about 25° C. and (b) at least one monomer wherein when said monomer is polymerized as a homopolymer having a Tg of from above about 25° C. to about 250° C. The polysiloxane moieties can be substituted on the polymer or can be made by co-polymerization of polysiloxane-containing polymerizable monomers (e.g. ethylenically unsaturated monomers, ethers, and/or epoxides) with non-polysiloxane-containing polymerizable monomers.

The polysiloxane-grafted polymer should have a weight average molecular weight of at least about 20,000. There is no upper limit for molecular weight except that which limits applicability of the invention for practical reasons, such as processing, aesthetic characteristics, formulateability, etc. In general, the weight average molecular weight will be less than about 10,000,000, more generally less than about 5,000,000, and typically less than about 3,000,000. Preferably, the weight average molecular weight will be between about 50,000 and about 2,000,000, more preferably between about 75,000 and about 1,000,000, most preferably between about 100,000 and about 750,000.

Preferably, the adhesive hereof when dried to form a film have a Tg of at least about −20° C., more preferably at least about −5° C., so that they are not unduly sticky, or "tacky" to the touch. As used herein, the abbreviation "Tg" refers to the glass transition temperature of the backbone of the polymer, if such a transition exists for a given polymer. Preferably, the Tg is above about −20° C., more preferably above about −5° C. Preferably the adhesive polymer of the present invention has a Tg below about 60° C., more preferably below about 50° C. and most preferably below about 40° C.

The silicone grafted polymers for the compositions of the present invention comprise "silicone-containing" (or "polysiloxane-containing") monomers, which form the silicone macromer pendant from the backbone, and non-silicone-containing monomers, which form the organic backbone of the polymer.

When used in a composition, such as a personal care composition for application to the hair or skin, the non-polysiloxane portion should permit the polymer to deposit on the intended surface, such as hair or skin.

The polysiloxane macromer should have a weight average molecular weight of at least about 1000, preferably from about 1,000 to about 50,000, more preferably from about 5,000 to about 50,000, most preferably about 8,000 to about 25,000. Organic backbones contemplated include those that are derived from polymerizable, ethylenically unsaturated monomers, including vinyl monomers, and other condensation monomers (e.g., those that polymerize to form polyamides and polyesters), ring-opening monomers (e.g., ethyl oxazoline and caprolactone), etc.

The preferred silicone grafted polymers are comprised of monomer units derived from: at least one free radically polymerizable ethylenically unsaturated monomer or monomers and at least one free radically polymerizable polysiloxane-containing ethylenically unsaturated monomer or monomers.

Vinyl Monomer Units

The silicone copolymers of the present invention comprise from about 50% to about 98%, preferably from about 60% to about 95%, and more preferably from about 70% to about 90% by weight of the vinyl monomer units.

The vinyl monomer unit is selected from copolymerizable monomers, preferably ethylenically unsaturated monomers. The vinyl monomers are selected to meet the requirements of the copolymer. By "copolymerizable", as used herein, is meant that the vinyl monomer can be reacted with or polymerized with the polysiloxane macromonomers in a polymerization reaction using one or more conventional synthetic techniques, such as ionic, emulsion, dispersion, Ziegler-Natta, free radical, group transfer or step growth polymerization. In the present invention, monomers and macromonomers that are copolymerizable using conventional free radical initiated techniques are preferred. The term "ethylenically unsaturated" is used herein to mean a material that contains at least one polymerizable carbon-carbon double bond, which can be mono-, di-, tri- or tetra-substituted.

The monomer units can be derived from hydrophilic monomers (typically polar monomers), or mixtures of such hydrophilic monomers with hydrophobic monomers (typically low polarity monomers), provided that the solubility characteristics of the overall copolymer is achieved. As used herein, "hydrophilic monomers" means monomers which form homopolymers which are substantially water soluble; "hydrophobic monomers" means monomers which form substantially water insoluble homopolymers.

Nonlimiting classes of monomers useful herein include monomers selected from the group consisting of unsaturated alcohols, unsaturated monocarboxylic acids, unsaturated dicarboxylic acids, unsaturated anhydrides, alcohol esters of unsaturated monocarboxylic acids, alcohol esters of unsaturated dicarboxylic acids, alcohol esters of unsaturated anhydrides, alkoxylated esters of unsaturated monocarboxylic acids, alkoxylated esters of unsaturated dicarboxylic acids, alkoxylated esters of unsaturated anhydrides, aminoalkyl esters of unsaturated monocarboxylic acids, aminoalkyl esters of unsaturated dicarboxylic acids, aminoalkyl esters of unsaturated anhydrides, amides of unsaturated monocarboxylic acids, amides of unsaturated dicarboxylic acids, amides of unsaturated anhydrides, salts of unsaturated monocarboxylic acids, salts of unsaturated dicarboxylic acids, salts of unsaturated anhydrides, unsaturated hydrocarbons, unsaturated heterocycles, and mixtures thereof.

Representative examples of such monomers include acrylic acid, methacrylic acid, N,N-dimethylacrylamide, dimethylaminoethyl methacrylate, quaternized dimethylaminoethyl methacrylate, methacrylamide, N-t-butyl acrylamide, maleic acid, maleic anhydride and its half esters, crotonic acid, itaconic acid, acrylamide, acrylate alcohols, hydroxyethyl methacrylate, diallyldimethyl ammonium chloride, vinyl pyrrolidone, vinyl ethers (such as methyl vinyl ether), maleimides, vinyl pyridine, vinyl imidazole, other polar vinyl heterocyclics, styrene sulfonate, allyl alcohol, vinyl alcohol (such as that produced by the hydrolysis of vinyl acetate after polymerization), vinyl caprolactam, acrylic or methacrylic acid esters of $C_1$–$C_{18}$ alcohols, such as methanol, ethanol, methoxy ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol(2-methyl-2-propanol), cyclohexanol, neodecanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-trimethyl-1-hexanol, 1-decanol, 1-dodecanol, 1-hexadecanol, 1-octadecanol, and the like, the alcohols having from about 1–18 carbon atoms with the number of carbon atoms preferably being from about 1–12; dicyclopentenyl acrylate; 4-biphenyl acrylate; pentachlorophenyl acrylate; 3,5-dimethyladamantyl acrylate; 3,5-dimethyladamentyl methacrylate; 4-methoxycarbonylphenyl methacrylate; trimethylsilyl methacrylate; styrene; alkyl substituted styrenes including alpha-methylstyrene and t-butylstyrene; vinyl esters, including vinyl acetate, vinyl neononanoate, vinyl pivalate and vinyl propionate; vinyl chloride; vinylidene chloride; vinyl toluene; alkyl vinyl ethers, including isobutyl vinyl ether and s-butyl vinyl ether; butadiene; cyclohexadiene; bicycloheptadiene; 2,3-dicarboxylmethyl-1,6-hexadiene; ethylene; propylene; indene; norbornylene; β-pinene; α-pinene; salts of acids and amines listed above, and combinations thereof. The quaternized monomers can be quaternized either before or after the copolymerization with other monomers of the graft copolymer.

Preferred monomers include acrylic acid, methacrylic acid, N,N-dimethyl acrylamide, dimethylaminoethyl methacrylate, quaternized dimethylaminoethyl methacrylate, vinyl pyrrolidone, acrylic or methacrylic acid esters of $C_1$–$C_{18}$ alcohols, styrene, alpha-methylstyrene, t-butylstyrene, vinyl acetate, vinyl propionate, 2-methoxyethyl acrylate, 2-ethoxyethyl acrylate, n-butyl methacrylate, isobutyl methacrylate, t-butyl acrylate, t-butyl methacrylate, 2-ethylhexyl methacrylate, methyl methacrylate, salts of any acids and amines listed above, and mixtures thereof.

From the above descriptions, esters of acrylic and methacrylic acid that form low Tg homopolymers include, for example, 3-methoxybutyl acrylate, 2-methoxyethyl acrylate, 2-phenoxyethyl acrylate, 2-hydroxyethyl acrylate, 4-hydroxybutyl acrylate, 2-ethoxyethoxyethyl acrylate, 2-ethoxyethyl acrylate, n-butyl acrylate, dodecyl acrylate, 2-ethylhexyl acrylate, 2-ethylbutyl acrylate, ethyl acrylate, n-heptyl acrylate, n-hexyl acrylate, iso-butyl acrylate, iso-decyl acrylate, iso-propyl acrylate, 3-methylbutyl acrylate, 2-methylpentyl acrylate, nonyl acrylate, octyl acrylate, 2-ethylhexyl methacrylate, n-pentyl methacrylate; Acrylamide monomers including N-dodecylacrylamide, N-octadecylacrylamide; Vinyl monomers including sec-butyl vinyl ether, butyl vinyl ether, vinyl propionate, vinyl butyrate, decylvinyl ether, methyl vinyl ether and styrene monomers including 4-decylstyrene. Other monomers that form low Tg homopolymers include isobutylene, 1-butene, 5-methyl-1-hexene, olefinic monomers that could be hydrogenated post polymerization (after formation of copolymers), for example, isoprene, 1,2-butadiene, 1,4-butadiene.

Preferred monomers which form low Tg homopolymers include 3-methoxybutyl acrylate, 2-methoxyethyl acrylate, n-butyl acrylate, 2-ethylhexyl acrylate, 2-ethylbutyl acrylate, n-heptyl acrylate, n-hexyl acrylate, iso-butyl acrylate, iso-decyl acrylate, iso-propyl acrylate, 3-methylbutyl acrylate, 2-methylpentyl acrylate, nonyl acrylate, octyl acrylate, N-octadecylacrylamide.

Most Preferred monomers which form low Tg homopolymers include 2-methoxyethyl acrylate and n-butyl acrylate. These low Tg monomers preferably have Tg of from about −70° C. to about 25° C., more preferably from about −60° C. to about 0° C. and most preferably from about −60° C. to about −20° C.

From the above descriptions, acrylic and methacrylic acids, and esters thereof, that form high Tg homopolymers include, for example, sec-butyl methacrylate, t-butyl acrylate, methyl methacrylate, isopropyl methacrylate, 2-t-butylaminoethyl methacrylate, dimethyl aminoethyl methacrylate, quaternized dimethyl aminoethyl methacrylate, 4-biphenyl acrylate, pentachlorophenyl acrylate, 3,5-dimethyladamantyl acrylate, 3,5-dimethyladamentyl methacrylate, isobornyl acrylate, trimethysilyl methacrylate, trimethylsilyl acrylate (silyl esters could be hydrolysed to form acrylic or methacrylic acids), acrylic acid, methacrylic acid, salts of acrylic and methacrylic acids; Acrylamide & methacrylamide monomers including N-butylacrytlamide, acrylamide, N-isopropylacrylamide, N-t-butylmethacrylamide; Vinyl monomers including: 2-vinylpyridine, 4-vinylpyridine, vinyl acetate, vinyl chloride, N-vinylcaprolactam, N-vinyl pyrollidone, cyclohexyl vinyl ether, vinyl alcohol, vinyl imidazole; Styrene monomers including: styrene, 4-t-butylstyrene, 2-methoxystyrene, 4-acetylstyrene, styrene sulfonate. Other monomers that form high Tg homopolymers include: diallyldimethylammonium chloride, maleimides, crotonic acid, itaconic acid, maleic anhydrides, allyl alcohol, α-pinene, β-pinene, tert-butyl styrene, α-methyl styrene, indene, norbornene, norbornylene.

Preferred monomers which form high Tg homopolymers include: t-butyl methacrylate, t-butyl acrylate, dimethyl aminoethyl methacrylate, isopropyl methacrylate, trimethysilyl methacrylate, trimethylsilyl acrylate, acrylic acid, methacrylic acid, salts of acrylic and methacrylic acids, N-isopropylacrylamide, N-t-butylmethacrylamide.

Most Preferred monomers which form high Tg homopolymers include: t-butyl methacrylate, t-butyl acrylate, acrylic acid, methacrylic acid, salts of acrylic and methacrylic acids. These high Tg monomers preferably have Tg of from about 25° C. to about 250° C., more preferably from about 30° C. to about 200° C. even more preferably from about 35° C. to about 150° C., and most preferably from about 40° C. to about 130° C.

Polysiloxane Macromonomer Units

The copolymers of the present invention comprise from about 2% to about 50%, preferably from about 5% to about 40%, and more preferably from about 10% to about 30%, by weight of the copolymer of polysiloxane macromonomer units.

The polysiloxane macromonomer units are copolymerizable with the vinyl monomers, said macromonomers preferably having a vinyl moiety. Either a single type of macromonomer unit or combinations or two or more macromonomer units can be utilized herein. The macromonomers are selected to meet the requirements of the copolymer. By "copolymerizable", as used herein, is meant that the macromonomers can be reacted with or polymerized with the vinyl monomers in a polymerization reaction using one or more conventional synthetic techniques, as described above.

The polysiloxane macromonomers that are useful herein contain a polymeric portion and a copolyermizable moiety which is preferably an ethylenically unsaturated moiety. Typically, the preferred macromonomers are those that are endcapped with the vinyl moiety. By "endcapped" as used herein is meant that the vinyl moiety is at or near a terminal position of the macromonomer.

The macromonomers can be synthesized utilizing a variety of standard synthetic procedures familiar to the polymer chemist of ordinary skill in the art. Furthermore, these macromonomers can be synthesized starting from commercially available polymers. Typically, the weight average molecular weight of the macromonomer is from about 1000 to about 50,000.

Polysiloxane macromonomers are exemplified by the general formula:

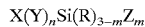

wherein X is a vinyl group copolymerizable with the vinyl monomer units; Y is a divalent linking group; each R is independently selected from the group consisting of hydrogen, hydroxyl, C1–C6 alkyl, C1–C6 alkoxy, C2–C6 alkylamino, phenyl, C1–C6 alkyl or alkoxy-substituted phenyl; Z is a monovalent siloxane polymeric moiety having a number average molecular weight of at least about 1000, is essentially unreactive under copolymerization conditions, and is pendant from the vinyl polymeric backbone described above; n is 0 or 1; and m is an integer from 1 to 3. The polysiloxane macromonomer has a weight average molecular weight from about 1000 to about 50,000, preferably from about 5,000 to about 30,000, more preferably from about 8,000 to about 25,000.

Preferably, the polysiloxane macromonomer has a formula selected from the following formulas:

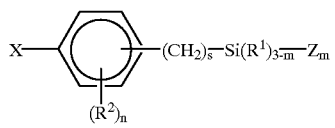

or

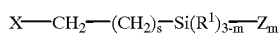

or

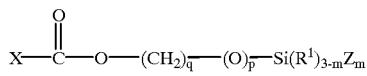

In these structures s is an integer from 0 to 6; preferably 0, 1, or 2; more preferably 0 or 1; m is an integer from 1 to 3, preferably 1; p is 0 or 1; q is an integer from 2 to 6; each $R^1$ is independently selected form the group consisting of hydrogen, hydroxyl, C1–C6 alkyl, C1–C6 alkoxy, C2–C6 alkylamino, phenyl, C1–C6 alkyl or alkoxy-substituted phenyl, preferably C1–C6 alkyl, or C1–C6 alkyl or alkoxy-substituted phenyl, more preferably C1–C6 alkyl, even more preferably methyl, $R^2$ is selected from the group consisting of C1–C6 alkyl or C1–C6 alkyl substituted phenyl, preferably methyl.

n is an integer from 0 to 4, preferably 0 or 1, more preferably 0; X is

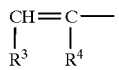

wherein $R^3$ is hydrogen or —COOH, preferably $R^3$ is hydrogen; $R^4$ is hydrogen, methyl or —CH$_2$COOH, preferably $R^4$ is methyl; Z is

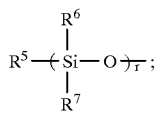

wherein $R^5$, $R^6$, and $R^7$, are independently selected from hydrogen, hydroxyl, C1–C6 alkyl, C1–C6 alkoooxy, C2–C6 alkylamino, phenyl, C1–C6 alkyl or alkooxy-substituted phenyl, hydrogen or hydroxyl, preferably $R^5$, $R^6$, and $R^7$ are C1–C6 alkyls; more preferably methyl; and r is an integer of from about 14 to about 700, preferably about 60 to about 400, and more preferably about 100 to about 350.

Exemplary silicone grafted polymers for use in the present invention include the following, where the composition is given as weight part of monomer used in the synthesis:

(i) poly(t-butyl acrylate-co-n-butyl acrylate-co-acrylic acid-co-methacrylic acid)-graft-poly(dimethylsiloxane)
MWt of copolymer: 210,000
Composition: t-butyl acrylate (36%), n-butyl acrylate (27%), acrylic acid (12%), methacrylic acid (10%), poly(dimethylsiloxane) (15%)
MWt of poly(dimethysiloxane): 10,000

(ii) poly(t-butyl acrylate-co-ethyl acrylate-co-acrylic acid)-graft-poly(dimethylsiloxane)
MWt of copolymer: 100,000
Composition: t-butyl acrylate (34%), ethyl acrylate (35%), acrylic acid (21%), poly(dimethylsiloxane) (10%)
MWt of poly(dimethylsiloxane): 5,000

(iii) poly(t-butyl acrylate-co-n-butyl acrylate-co-acrylic acid)-graft-poly(dimethylsiloxane)
MWt of copolymer: 150,000
Composition: t-butyl acrylate (47.25%), n-butyl acrylate (22.75%), acrylic acid (20%), poly(dimethylsiloxane) (10%)
MWt of poly(dimethylsiloxane): 10,000

(iv) poly(t-butyl acrylate-co-2-methoxyethyl acrylate-co-methacrylic acid)-graft-poly(dimethylsiloxane)
MWt of copolymer: 100,000
Composition: t-butyl acrylate (27%), 2-methoxyethyl acrylate (43%), methacrylic acid (20%), poly(dimethylsiloxane) (10%)
MWt of poly(dimethylsiloxane): 15,000

(v) poly(t-butyl acrylate-co-isobornyl acrylate-co-2-methoxyethyl acrylate-co-acrylic acid)-graft-poly(dimethylsiloxane)
MWt of copolymer: 95,000
Composition: t-butyl acrylate (33%), isobornyl acrylate (17%), 2-methoxyethyl acrylate (20%), acrylic acid (20%), poly(dimethylsiloxane) (1 0%)
MWt of poly(dimethylsiloxane): 10,000

(vi) poly(t-butyl acrylate-co-lauryl methacrylate-co-acrylic acid)-graft-poly(dimethylsiloxane)
MWt of copolymer: 125,000
Composition: t-butyl acrylate (60%), lauryl methacrylate (10%), acrylic acid (20%), poly(dimethylsiloxane) (10%)
MWt of poly(dimethylsiloxane): 15,000

The Tg's for monomer units above can be found in *The Polymer Handbook,* third edition, (John Wiley & Sons, New York, 1989) and the backbone Tg can be calculated using the method illustrated in *Fundamental Principles of Polymeric Materials,* second edition (John Wiley & Sons, New York, 1993). Representative Tg's for monomers in the exemplary silicone grafted polymers described above are as follows: The Tg of t-butyl acrylate is 44.85° C.; the Tg of n-butyl acrylate is −54.15° C.; the Tg of acrylic acid is 105.85° C.; the Tg of methacrylic acid is 227.85° C.; the Tg of ethyl acrylate is −24.15° C.; the Tg of lauryl methacrylate is −65.15° C.; and the Tg of 2-methoxyethyl acrylate is −50.15° C.

The silicone grafted polymers can be synthesized by free radical polymerization of the polysiloxane-containing monomers with the non-polysiloxane-containing monomers. The synthetic procedures are in general the same as those described for the adhesive copolymer. The silicone macromer is added in to the reactor along with the "A" and "B" monomers, and the reaction proceeds as for the adhesive copolymer examples. Compared to the adhesive copolymer, it may be necessary to choose different solvents for the polymerization reaction, as apparent to one skilled in the art, to keep the monomers and polymers in solution throughout the polymerization.

Without being limited by theory, it is believed that in forming the above-described silicone grafted polymers, there is some polymer which does not incorporate the silicone graft; such polymers have a relatively low weight average molecular weight e.g., below 20,000.

Optional Components

The compositions of the present invention can be formulated into personal care compositions, or any other composition in which an adhesive may be useful such as adhesive tapes, glues and the like.

Personal care compositions comprise from about 0.1% to about 99.9%, preferably from about 0.5% to about 99.0% and most preferably from about 1.0% to about 99.9% of a suitable personal care carrier. Suitable carriers are fully described in U.S. Pat. No. 5,061,481 issued Oct. 29, 1991 to Suzuki et al., incorporated by reference herein. For example, skin care carriers typically comprise oil-in-water emulsions.

Hair spray compositions typically comprise a polar solvent phase as a liquid vehicle for the silicone grafted polymer. The polar solvent phases comprise one or more polar solvents that are present in the hair care compositions at a level of from about 80% to about 99%, preferably from about 85% to about 98%, more preferably from about 90% to about 95% of the total composition.

If formulated as shampoos and rinse compositions, such compositions typically comprise a volatile, nonpolar, branched chain hydrocarbon and is safe for topical application to the skin and hair. The branched chain hydrocarbon solvent hereof is present at a level of from about 0.1% to about 15%, preferably from about 0.5% to about 10%, more preferably from about 2% to about 8%, by weight of the composition. Also useful are low boiling point silicone oils.

The branched chain hydrocarbon solvent is characterized by a boiling point of at least about 105° C., preferably at least about 110° C., more preferably at least about 125° C., most preferably at least about 150° C. The boiling point is also generally about 260° C. or less, preferably about 200° C. or less. The hydrocarbon chosen should also be safe for topical application to the hair and skin.

The branched chain hydrocarbon solvents are selected from the group consisting of $C_{10}$–$C_{14}$ branched chain hydrocarbons, and mixtures thereof, preferably $C_{11}$–$C_{13}$ branched chain hydrocarbons, more preferably $C_{12}$ branched chain hydrocarbons. Saturated hydrocarbons are preferred, although it is not necessarily intended to exclude unsaturated hydrocarbons.

Examples of suitable nonpolar solvents include isoparaffins of the above chain sizes. Isoparaffins are commercially available from Exxon Chemical Co. Examples include Isopar™ G ($C_{10}$–$C_{11}$ isoparaffins), Isopar™ H and K ($C_{11}$–$C_{12}$ isoparaffins), and Isopar™ L ($C_{11}$–$C_{13}$ isoparaffins). The most preferred nonpolar solvent are $C_{12}$ branched chain hydrocarbons, especially isododecane. Isododecane is commercially available from Preperse, Inc. (South Plainfield, N.J., USA) as Permethyl™ 99A.

Plasticizer

The compositions hereof can optionally contain a plasticizer for the silicone grafted polymer. Any plasticizer suitable for use in hair care products or for topical application to the hair or skin can be used. A wide variety of plasticizers are known in the art. These include acetyl triethylcitrate, triethycitrate, glycerin, diisobutyl adipate, butyl stearate, and propylene glycol. Plasticizers are typically used at levels of from about 0.01% to about 10%, by weight of the composition, preferably from about 0.05% to about 3%, more preferably from about 0.05% to about 1%.

Adhesive Polymer

The polymers of the present invention can be combined with an additional adhesive polymer to form adhesive compositions. The compositions hereof will generally comprise from about 0.1% to about 15%, preferably from 0.5% to about 8%, more preferably from about 1% to about 8%, by weight of the composition, of the adhesive polymer. It is not intended to exclude the use of higher or lower levels of the polymers, as long as an effective amount is used to provide adhesive or film-forming properties to the composition and the composition can be formulated and effectively applied for its intended purpose. By adhesive polymer what is meant is that when applied as a solution to a surface and dried, the polymer forms a film. Such a film will have adhesive and cohesive strength, as is understood by those skilled in the art.

The polymeric backbone is chosen such that it is compatible with the silicone adhesive styling polymer. By "compatible" is meant is that, when placed in a suitable solvent, the polymers form a stable solution, i.e., the polymers do not compete for solubility and therefore, cause no phase separation and when the solution is dried a uniform film is formed, with no macrophase separation of the two polymers. A suitable solvent is a solvent which substantially completely dissolves the non-silicone and silicone grafted polymers at the levels described herein. The polymer blend forms a relatively clear hairspray system (% transmittance at 450 nm is generally greater than 80%). It is recognized that certain plasticizers can form cloudy films as well as incorrect neutralization levels. Therefore, this would fall outside this definition of compatibility. The compatibility can be tested by dissolving the adhesive polymer and the silicone grafted hair styling resin in a mutual solvent, and then evaporating the solvent to form a film. Incompatible polymers will form a cloudy film with poor mechanical properties, due to the large scale phase separation of the two polymers. Alternatively, after drying the polymer solution to a film, compatibility can be evaluated by measuring the Tg. Compatible polymers will have a single Tg, while incompatible polymers will exhibit two Tg's. Although compatibility can occur between two polymers of completely different structures, it is preferred that compatibility be obtained by making the composition of the non-silicone backbone of the silicone grafted polymer similar to or identical to the composition of the adhesive polymer.

The adhesive polymer should have a weight average molecular weight of at least about 20,000, preferably greater than about 25,000, more preferably greater than about 30,000, most preferably greater than about 35,000. There is no upper limit for molecular weight except that which limits applicability of the invention for practical reasons, such as processing, aesthetic characteristics, formulateability, etc. In general, the weight average molecular weight will be less than about 10,000,000, more generally less than about 5,000,000, and typically less than about 2,000,000. Preferably, the weight average molecular weight will be between about 20,000 and about 2,000,000, more preferably between about 30,000 and about 1,000,000, and most preferably between about 40,000 and about 500,000.

Preferably, the adhesive hereof when dried to form a film have a Tg of at least about –20° C., more preferably at least about 20° C., so that they are not unduly sticky, or "tacky" to the touch. As used herein, the abbreviation "Tg" refers to the glass transition temperature of the backbone of the polymer. Preferably, the Tg is above about –20° C., more preferably above about 20° C.

Preferably the weight ratio of the non-silicone polymer to silicone grafted polymer ranges from about 1:10 to about 1:1, preferably from about 1:5 to about 1:1.

Exemplary adhesive polymers for use in the present invention include the following, where the numbers following the structure indicate the weight ratios of monomers as loaded into the polymerization reactor:

(i) acrylic acid/t-butyl acrylate 25/75

(ii) dimethylaminoethyl methacrylate/isobutyl methacrylate/2-ethylhexyl-methacrylate 40/40/20

(iii) t-butylacrylate/acrylic acid 65/35

(iv) polymer (ii) quaternized by treatment with methyl chloride

The adhesive polymers can be synthesized as described above such as by free radical polymerization of the monomers.

Solubility of the adhesive polymer, as described above, should be determined after neutralization, if any, as well as after addition of other ingredients that may be included in the polar solvent phase, such as surfactants, solubilizers, etc.

The present compositions can contain a wide variety of additional optional ingredients, including among them any of the types of ingredients known in the art for use in hair setting compositions, especially hair spray compositions and hair setting tonics. These ingredients include, but are not limited to, surfactants (including fluorinated surfactants and silicone copolyols), and ionic strength modifiers, propellants, hair conditioning agents (e.g., silicone fluids, fatty esters, fatty alcohols, long chain hydrocarbons, cationic surfactants, etc.).

Ionic Strength Modifier System

Optionally, compositions made from the polymers of the present invention can contain an effective amount of a non-surface active ionic strength modifier system for reducing the viscosity of the hair spray composition. When used, the ionic strength modifiers will be present in the present compositions at a level of at least about 0.01%, by weight of the composition. The upper limit is dependent upon the maximum amount of the ionic strength modifiers that can be present in the particular compositions hereof such that the hair setting resin remains solubilized or dispersed. As will be understood by those skilled in the art, as the ionic strength of the composition is increased, the resin will eventually fall out of solution, or otherwise no longer remain solubilized or dispersed in the polar liquid carrier. The upper limit of the ionic strength modifier system level will vary depending upon the particular ionic strength modifiers, liquid vehicle, resin, and other ingredients present in the composition. Thus, for example, the maximum amount of the ionic strength modifiers that can be used will tend to be lower for compositions with liquid vehicles containing less water, compared to compositions with more water. Generally, the compositions will comprise about 4%, by weight, or less of the ionic strength modifiers, more generally about 2% or less, and typically about 1% or less. Preferably, the compositions hereof will comprise from about 0.01% to about 0.5%, more preferably from about 0.01% to about 0.1%, of the ionic strength modifier system.

The ionic strength modifier system comprises a mixture of monomeric cations and anions. The ions of the ionic strength modifier system hereof are non-surface active, i.e. they do not significantly reduce surface tension. For purposes hereof, non-surface active shall mean the ions, which at a 0.5% aqueous solution concentration, reduce surface tension by no more than 5.0 dynes/cm2. Generally, the ions of the ionic strength modifier system hereof will be characterized by having, at maximum, four or less carbon atoms per charge, preferably two or less carbon atoms, in any aliphatic chain or straight or branched chain organic heterochain.

The ionic strength modifier system comprises monomeric ions of the type which are products of acid-base reactions. Thus, basic and acidic ions $OH^-$ and $H^+$ do not constitute part of the ionic strength modifier system hereof, although they may be present in the composition. The ions hereof are incorporated into the composition in a form such that they can exist in the composition as free ions, i.e., in dissociated form. It is not necessary that all of the ions added exist in the composition as free ions, but must be at least partially soluble or dissociated in the composition. The ionic strength modifiers can be incorporated into the hair styling compositions, for example, by addition of soluble salts, or by addition of mixtures of acids and bases, or by a combination thereof. It is a necessary aspect of the invention that both anions and cations of the ionic strength modifier system be included in the composition.

Suitable cations for use include, for example, alkali metals, such as lithium, sodium, and potassium, and alkaline-earth metals, such as magnesium, calcium, and strontium. Preferred of the divalent cations is magnesium. Preferred monovalent metal ions are lithium, sodium, and potassium, particularly sodium and potassium. Suitable means of addition to the compositions hereof include, for example, addition as bases, e.g., hydroxides, sodium hydroxide and potassium hydroxide, and such as salts that are soluble in the liquid carrier, e.g. salts of monomeric anions such as those described below.

Other suitable cations include organic ions, such as quaternary ammonium ions and cationic amines, such as ammonium mono-, di-, and tri-ethanolamines, triethylamine, morpholine, aminomethylpropanol (AMP), aminoethylpropanediol, etc. Ammonium and the amines are preferably provided in the forms of salts, such as hydrochloride salts.

Monomeric anions that can be used include halogen ions, such as chloride, fluoride, bromide, and iodide, particularly chloride, sulfate, ethyl sulfate, methyl sulfate, cyclohexyl sulfamate, thiosulfate, toluene sulfonate, xylene sulfonate, citrate, nitrate, bicarbonate, adipate, succinate, saccharinate, benzoate, lactate, borate, isethionate, tartrate, and other monomeric anions that can exist in dissociated form in the hair styling composition. The anions can be added to the compositions hereof, for example, in the form of acids or salts which are at least partially soluble in the liquid vehicle, e.g., sodium or potassium salts of acetate, citrate, nitrate, chloride, sulfate, etc. Preferably, such salts are entirely soluble in the vehicle.

The use of ionic strength modifiers are especially useful in reduced volatile organic solvent compositions, most especially those utilizing silicone macromer-containing polymers.

Personal Care Compositions

The polymers of the present invention can be incorporated into a wide variety of personal care compositions, including shampoos, soaps, lotions, creams, antiperspirants, nail enamels, lipsticks, foundations, mascaras, sunscreens, hair spray compositions, mousses, and hair setting tonics. Compositions that will be flowable, e.g., low viscosity compositions that, preferably, are suitable for spray application as well as higher viscosity compositions are also contemplated.

Personal care carriers are suitable for use in the present invention are described in U.S. Pat. No. 5,306,485 to Robinson et al., issued Apr. 26, 1994, and U.S. Pat. No. 5,002,680 to Schmidt et al., issued Mar. 26, 1991, both of which are incorporated by reference herein. The following Experimentals and Examples further illustrate embodiments within the scope of the present invention. They are given solely for the purposes of illustration and are not to be construed as limitations of the present invention as many variations of the invention are possible without departing from its spirit and scope.

EXAMPLES

The following examples exemplify silicone grafted polymers of the present invention.

Example 1
Synthesis of Poly(t-butyl acrylate-co-n-butyl acrylate-co-acrylic acid-co-methacrylic acid)-graft-poly(dimethylsiloxane)

Place 42.75 parts of t-butyl acrylate, 27.25 parts n-butyl acrylate, 10 parts methacrylic acid, 10 parts acrylic acid, and 10 parts polydimethylsiloxane macromonomer in a round-bottom flask. Add sufficient acetone as the reaction solvent to produce a final monomer concentration of 20%. Purge the vessel with argon for approximately one hour. Following the purge, maintain a constant positive pressure on the closed reaction system with argon. Heat the reaction to 58° C. Prepare a 10% solution of azobisisobutyronitrile (0.5% by weight relative to the amount of monomer) in acetone, and add it to the reaction mixture. Maintain heat and stirring for 20 hours. Terminate the reaction by opening the reactor to atmosphere and cooling to room temperature.

The polymer solution is then precipitated in water at one part solution to 15 parts water. The resultant polymer is then redissolved in acetone. This procedure is repeated six times, with the final polymer being placed in a vacuum oven for heated drying. This completes the polymer purification process.

Example 2
Synthesis of Poly(t-butyl acrylate-co-n-butyl acrylate-co-methacrylic acid)-graft-poly(dimethylsiloxane)

Place 32 parts of t-butyl acrylate, 27 parts n-butyl acrylate, 21 parts methacrylic acid, and 20 parts polydimethylsiloxane macromonomer in a roundbottom flask. Add sufficient acetone as the reaction solvent to produce a final monomer concentration of 20%. Purge the vessel with argon for approximately one hour. Following the purge, maintain a constant positive pressure on the closed reaction system with argon. Heat the reaction to 58° C. Prepare a 10% solution of azobisisobutyronitrile (0.5% by weight relative to the amount of monomer) in acetone, and add it to the reaction mixture. Maintain heat and stirring for 20 hours. Terminate the reaction by opening the reactor to atmosphere and cooling to room temperature.

The polymer solution is then precipitated in water at one part solution to 15 parts water. The resultant polymer is then redissolved in acetone. This procedure is repeated six times, with the final polymer being placed in a vacuum oven for heated drying. This completes the polymer purification process.

What is claimed is:

1. A polymer for use in personal care compositions comprising a silicone grafted adhesive polymer having a Tg of from about −20° C. to about 60° C., said adhesive polymer being characterized by an organic polymeric backbone wherein said backbone comprises
   (a) at least one low Tg monomer wherein when said low Tg monomer is polymerized as a homopolymer, said homopolymer has a Tg of from about −120° C. to about −20 ° C.; and wherein the low Tg monomer is selected from the group consisting of 3-methoxybutyl acrylate, 2-methoxyethyl acrylate, n-butyl acrylate, 2-ethylhexyl acrylate, 2-ethylbutyl acrylate, n-heptyl acrylate, n-hexyl acrylate, iso-butyl acrylate, iso-decyl acrylate, iso-propyl acrylate, 3-methylbutyl acrylate, 2-methylpentyl acrylate, nonyl acrylate, octyl acrylate, N-octadecylacrylamide and mixtures thereof; and
   (b) at least two high Tg monomers wherein when each high To monomer is polymerized as a homopolymer said homopolymer has a Tg of from about 25° C. to about 250° C., wherein the high Tg monomers of are selected from the group consisting of t-butyl methacrylate, t-butyl acrylate, dimethyl aminoethyl methacrylate, isopropyl methacrylate, trimethysilyl methacrylate, trimethylsilyl acrylate, acrylic acid, methacrylic acid, salts of acrylic and methacrylic acids, N-isopropylacrylamide, N-t-butylmethacrylamide and mixtures thereof; and wherein at least one of said high Tg monomers is selected from the group consisting of acrylic acid and methacrylic acid monomers; and one of the high Tg monomers is t-butyl acrylate; and
   wherein said silicone grafted adhesive polymer has silicone macromers grafted to said backbone; and wherein the number average molecular weight of said silicone macromers is greater than about 1000.

2. A polymer according to claim 1 wherein the low Tg monomer is selected from the group consisting of 2-methoxyethyl acrylate, n-butyl acrylate, and mixtures thereof.

3. A polymer according to claim 1 wherein the low Tg monomer has a Tg of from about −60° C. to about −20° C.

4. A polymer according to claim 1 wherein the high Tg monomer is selected from the group consisting of t-butyl methacrylate, t-butyl acrylate, acrylic acid, methacrylic acid, and salts of acrylic and methacrylic acids.

5. A polymer according to claim 4 wherein the high Tg monomer has a Tg of from about 30° C. to about 200° C.

6. A polymer according to claim 5 wherein the high Tg monomer has a Tg of from about 35° C. to about 150° C.

7. A polymer according to claim 4 wherein the high Tg monomer has a Tg of from about 40° C. to about 130° C.

8. A polymer according to claim 1 wherein said copolymer is formed from the random copolymerization of the following relative weight percentages of low Tg and high Tg monomers and polysiloxane-containing macromonomer units:
   a. from about 50% to about 98%, by weight of said copolymer, of low Tg and high Tg monomers, and
   b. from about 2% to about 50%, by weight of said copolymer, of polysiloxane-containing macromonomer units, wherein said polysiloxane-containing macromonomer units have a weight average molecular weight from about 1,000 to about 50,000, and correspond to the chemical formula:

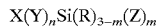

wherein:

X is a vinyl group copolymerizable with said low Tg and high Tg monomers;

Y is a divalent linking group;

R is selected from the group consisting of hydrogen, hydroxyl, C1–C6 alkyl, C1–C6 alkoxy, C2–C6 alkylamino, phenyl, C1–C6 alky or alkoxy-substituted phenyl;

Z is a monovalent siloxane polymeric moiety having a number average molecular weight of at least about 1000, is essentially unreactive under copolymerization conditions, and is pendant from said vinyl polymeric backbone after polymerization;

n is 0 or 1; and m is an integer from 1 to 3.

* * * * *